United States Patent [19]

Zimmermann

[11] 4,301,795
[45] Nov. 24, 1981

[54] VACCINATION GUN

[75] Inventor: Josef Zimmermann, Sulzbach, Fed. Rep. of Germany

[73] Assignee: Hoechst Aktiengesellschaft, Frankfurt am Main, Fed. Rep. of Germany

[21] Appl. No.: 86,127

[22] Filed: Jul. 19, 1979

[30] Foreign Application Priority Data

Jul. 22, 1978 [DE] Fed. Rep. of Germany ....... 2832252

[51] Int. Cl.³ .............................................. A61M 5/30
[52] U.S. Cl. ........................... 128/207.25; 222/402.2; 222/335
[58] Field of Search ...................... 128/200.23, 207.23, 128/207.25, 205.21, 213 R, 218 A, 203.15; 222/402.2, 335

[56] References Cited
U.S. PATENT DOCUMENTS

| | | | |
|---|---|---|---|
| 2,358,719 | 9/1944 | Klein | 222/335 |
| 2,574,028 | 11/1951 | Fields et al. | 128/205.21 X |
| 3,250,444 | 5/1966 | Ward | 222/402.2 |
| 3,292,622 | 12/1966 | Banker | 128/207.25 |
| 3,394,851 | 7/1968 | Gorman | 222/402.2 |
| 3,518,990 | 7/1970 | Banker | 128/207.25 |

*Primary Examiner*—Henry J. Recla
*Attorney, Agent, or Firm*—Curtis, Morris & Safford

[57] ABSTRACT

In a vaccination gun provided with a piston pump for the vaccine and a gas-propelled motor for the vaccine pump, the drive motor is arranged with one end thereof coupled to the vaccine pump. In the handle grip of the vaccination gun, a coupler connects a propellant gas cylinder, through a trigger, or locking valve, to the drive motor. In order to assure that the injection pressure of the propellant gas remains between about 270 and 300 bar regardless of the pressure in the cylinder, there is provided a pressure regulation chamber between the coupler and the locking valve, which chamber is provided with a flap valve coupled to a hollow shaft. The shaft moves within a cylindrical portion of the chamber and is provided with radial borings for permitting the propellant gas to pass between the main part of the chamber and the cylindrical portion thereof.

7 Claims, 4 Drawing Figures

VACCINATION GUN

BACKGROUND OF THE INVENTION

The invention relates to a vaccination gun for medicinal purposes, and particularly to such a gun which is provided with an arrangement to maintain the gas pressure for the drive motor of the vaccine pump substantially constant.

In claim 1 of German Patent Specification 1 922 569 a vaccination gun is described in which the vaccine pump is operated by a motor driven by gas. This gun has the disadvantage that with differing gas pressures, caused, for example, by changing gas pressures in the gas storage container, the motor transfers different forces on the vaccine pump and thus causes, in dependence of the gas pressure, the vaccine to be injected at varying depths into the tissue. For medicinal reasons, however, the injection pressures at the muzzle of the vaccine nozzle should not exceed about 270–300 bar. However, a freshly filled gas bottle produces injection pressures of up to about 750 bar, so that the vaccine is projected far deeper than is safe or desirable into the tissue.

OBJECTS AND SUMMARY OF THE INVENTION

An object of this invention is to improve the vaccination gun of the above-mentioned type to insure that the injection pressure at the muzzle of the vaccine nozzle is between 270 and 300 bar over its entire working range.

The present invention, as typified in the ensuing embodiment, solves this task by providing a chamber installed between the locking valve and a coupler to the propellant gas container which is provided with a flap-valve having a hollow shaft protruding into a part of the chamber and which is provided with radial borings.

In order to equalize the pressure on opposite sides of the flap-valve after effected injection shot, the valve face may be provided with a leakage arrangement in the form of a narrow boring or groove so that the gas of the store bottle or cylinder can gradually pass to the locking valve. However, pressure equalization may also be effected through a bypass line, in which a valve may be installed. The flap-valve can also be opened mechanically, for example by means of the trigger device. This trigger device is arranged at that part of the chamber into which the shaft of the flap-valve projects.

The invention is illustrated by the annexed drawings which show just one embodiment:

DETAILED DESCRIPTION OF A PREFERRED EMBODIMENT

Figure 1:
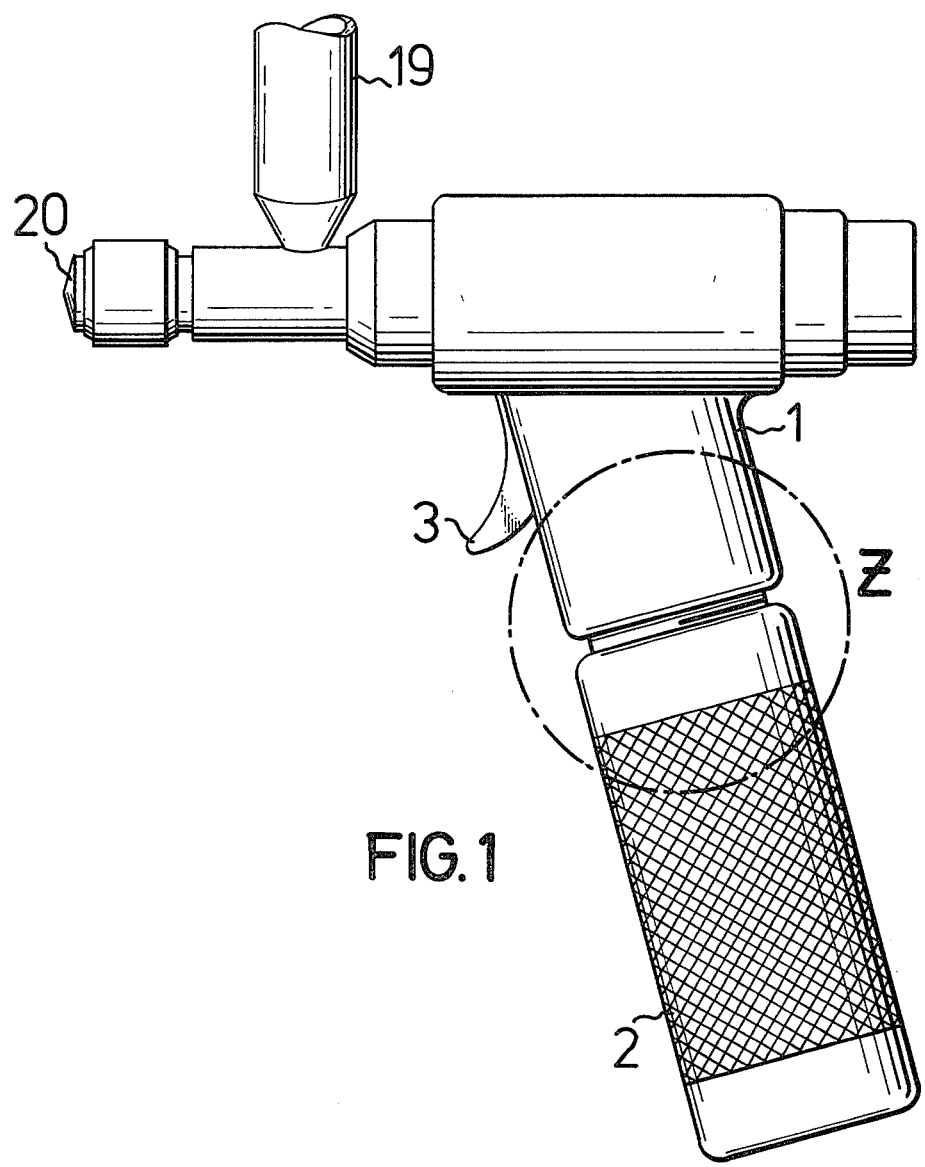
FIG. 1 is a side elevation of a vaccination gun according to an embodiment of this invention.
Figure 2:
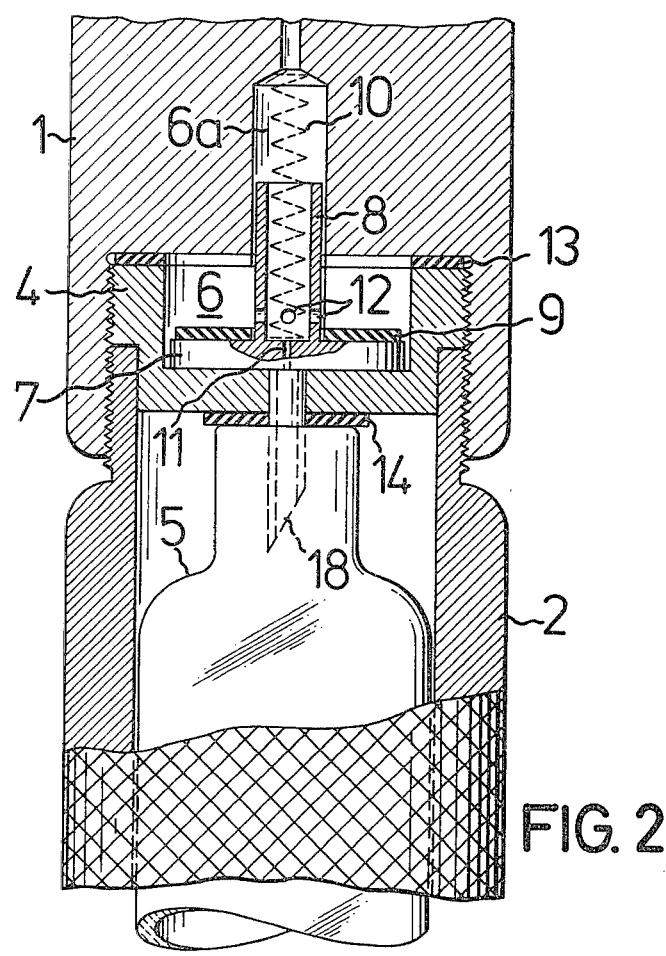
FIG. 2 is a sectional detail view of the portion Z of FIG. 1.
Figure 3:
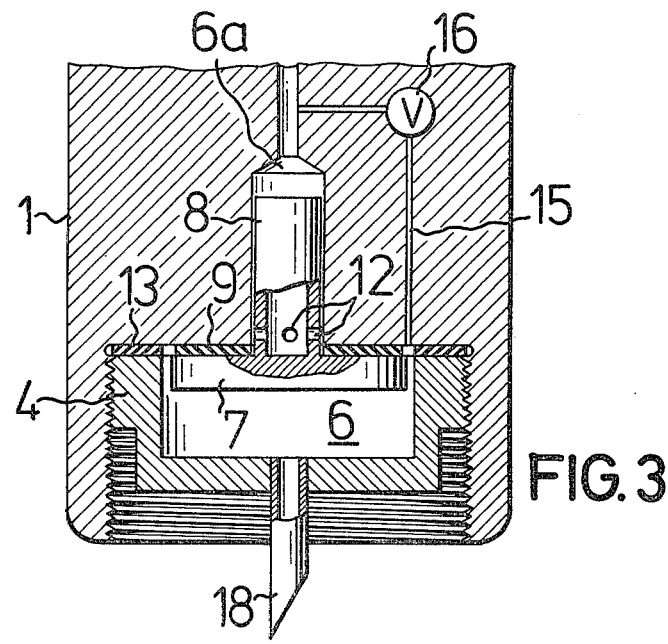
FIG. 3 shows a bypass arrangement for equalizing the propellant gas pressure for the flap-valve in the embodiment of FIG. 1.
Figure 4:
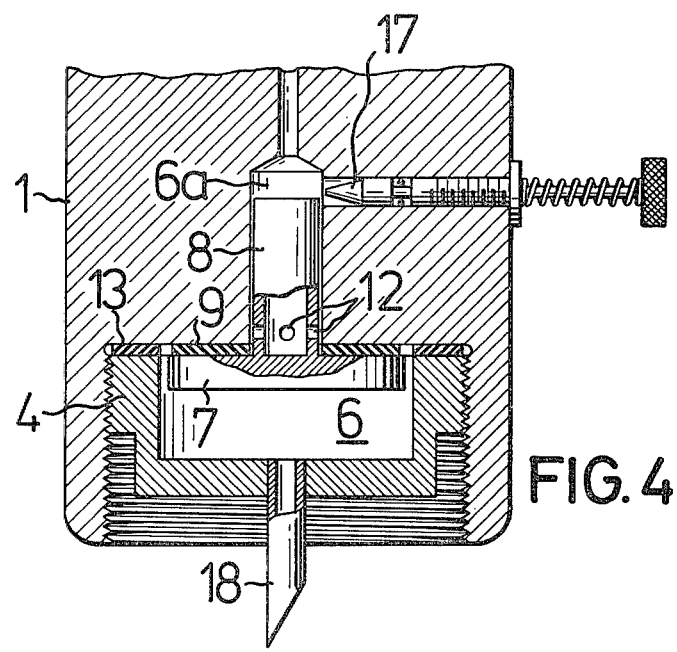
FIG. 4 shows a trigger arrangement for equalizing the propellant gas pressure.

With reference to the drawings, according to an embodiment of the vaccination gun of this invention, the gun grip thereof is formed of a flange (1) and a grip (2) which can be screwed into flange (1). Flange (1) houses the locking valve (3) for triggering the release of the propellant gas to the drive motor and a coupler (4) for connecting to a propellant gas container or cylinder (5) for the gas. Coupler (4) is so designed as to form a chamber (6, 6a) with flange (1), having a first portion (6) near cylinder (5) and a second portion (6a) extending toward the locking valve (3). A flap-valve (7) with a hollow shaft (8) is arranged within this chamber (6, 6a). The shaft (8) projects into the cylindrical second portion (6a) of the chamber (6, 6a). Furthermore, flap-valve (7) is provided with a sealing device (9) such as a gasket, at the side facing flange (1) and may also have a leakage arrangement (11). A pressure spring (10) may be installed within the interior of shaft (8) to bias the flap-valve (7) away from the second portion (6a) of the chamber. In order to permit the gas to escape in the direction toward the motor, shaft (8) is provided with borings (12). The coupler (4) is held tightly against flange (1) by means of seal or gasket (13) and the propellant gas container (5) is secured tightly to the connecting piece (4) by means of seal (14). The leakage arrangement (11)—here a boring—is so dimensioned that gas leaks through relatively slowly and no noticeable pressure equalization between the two sides of the flap-valve (7) takes place during the injection shot. Grip (2) may house a cylinder (5), as shown, for the gas. However, the cylinder (5) may also be replaced by an adapter for other gas containers. The symbol (18) indicates the fitting for cylinder (5). The symbol (19) indicates the container of the vaccine and (20) the nozzle for the vaccine.

In order to completely fill the chamber (6, 6a) with gas after having shot an injection, it is necessary to open the flap-valve (7). For this purpose, pressure equalization between the two sides of flap-valve (7) must take place. This can be done, as already mentioned, through leakage arrangement (11). However, it is also possible to provide sealing gasket (9) with a thin radial groove. Part (6a) of the chamber (6, 6a) may also be connected with a bypass line (15) which is provided with a valve (16). A mechanical triggering device (17) for opening the valve flap (7) may also project into part (6a) of the chamber (6, 6a).

Prior to the injection shot, the chamber (6, 6a) is filled with gas which is, of course under the same pressure as the propellant gas in store container (5). Upon opening of the locking valve (3), the gas from chamber (6, 6a) passes to the drive motor of the vaccine pump (not shown). Flap-valve (7) is pressed at its sealing gasket (9) against flange (1) by the relatively high pressure gas coming from the store container (5), so that any afterflow of gas from the store container (5) to the drive motor is prevented. Then the gun is prepared for the next shot by equalization of pressure on the two sides of the flap-valve (7) so that the latter is opened.

What is claimed is:

1. In a vaccination gun of the type having a vaccine piston pump, drive motor means for driving the pump, said drive motor means being operated by a propellant gas, locking valve means for selectively admitting said propellant gas to said drive motor means, container means for holding said propellant gas, coupler means for coupling said container means with said locking valve means, and housing means housing said container means and coupler means and forming a gun grip; the improvement wherein said coupler means includes a chamber fluidically connected between said container means and said locking valve means, flap-valve means loosely a chamber and slidably mounted in said chamber and dividing said chamber into a first portion communicating with said container means and a second portion communicating with said locking valve means, said flap-valve means being responsive to pressure released by said locking valve means to move from a first position in said chamber adjacent said container means to a second position in said chamber adjacent said locking means, said coupler means including means for providing a gas leak from said first portion to said second portion of said chamber; and wherein said chamber includes means for sealing against said flap-valve means when in said second position thereby preventing gas flow from said first portion to said second portion except through said means for providing a gas leak whereby, pressure between the first and second portions of the chamber is equalized after said flap-valve means is sealed against said sealing means; and biasing means biasing said flap valve means away from said sealing means and toward said first position after said pressure is equalized.

2. A vaccination gun according to claim 1, wherein said second portion of said chamber is diametrically smaller than the first portion and said flap-valve means includes a piston loosely and slidably mounted in said first portion and a hollow shaft extending axially from said piston and being loosely and slidably mounted in said second portion and wherein said hollow shaft includes at least one radial bore communicating the interior of said shaft with said second portion of said chamber.

3. A vaccination gun according to claim 2, wherein said means for providing a leak includes a bore extending through said piston into said hollow shaft to equalize pressure on opposite sides of said flap-valve means.

4. A vaccination gun according to claim 2, wherein said biasing means includes a pressure spring mounted within said hollow shaft and between said piston and chamber.

5. A vaccination gun according to claim 1, wherein said means to provide a leak includes a bore extending through said flap-valve means to equalize pressure on opposite sides of said flap-valve means.

6. A vaccination gun according to claim 1 or 2, wherein said means for providing a gas leak includes a bypass line around said chamber connecting said first portion to said second portion to equalize the pressure on opposite sides of said flap-valve means.

7. A vaccination gun according to claim 5 or 6 wherein said means providing a gas leak includes mechanical trigger means for urging said flap-valve means toward said first position thereby providing a gas leak between said flap-valve means and said chamber.

* * * * *